US009757315B2

(12) United States Patent
Nakauchi et al.

(10) Patent No.: US 9,757,315 B2
(45) Date of Patent: *Sep. 12, 2017

(54) TOOTH WHITENER

(71) Applicant: Kao Corporation, Chuo-ku, Tokyo (JP)

(72) Inventors: Gen Nakauchi, Tokyo (JP); Yoshiyuki Eshita, Tokyo (JP); Keizo Takahashi, Tokyo (JP)

(73) Assignee: Kao Corporation, Tokyo (JP)

( * ) Notice: Subject to any disclaimer, the term of this patent is extended or adjusted under 35 U.S.C. 154(b) by 0 days.

This patent is subject to a terminal disclaimer.

(21) Appl. No.: 14/439,393

(22) PCT Filed: Oct. 31, 2013

(86) PCT No.: PCT/JP2013/079613
§ 371 (c)(1),
(2) Date: Apr. 29, 2015

(87) PCT Pub. No.: WO2014/069594
PCT Pub. Date: May 8, 2014

(65) Prior Publication Data
US 2015/0297479 A1    Oct. 22, 2015

(30) Foreign Application Priority Data
Oct. 31, 2012   (JP) ................. 2012-241306

(51) Int. Cl.
*A61K 8/24* (2006.01)
*A61K 8/03* (2006.01)
*A61K 8/21* (2006.01)
*A61Q 11/00* (2006.01)
*A61K 8/55* (2006.01)
*A61K 8/02* (2006.01)

(52) U.S. Cl.
CPC .............. *A61K 8/24* (2013.01); *A61K 8/0204* (2013.01); *A61K 8/03* (2013.01); *A61K 8/21* (2013.01); *A61K 8/55* (2013.01); *A61Q 11/00* (2013.01); *A61K 2800/884* (2013.01)

(58) Field of Classification Search
None
See application file for complete search history.

(56) References Cited

U.S. PATENT DOCUMENTS

| 3,897,548 | A | * | 7/1975 | Katz ................. A61K 8/21 424/54 |
| 4,363,794 | A | * | 12/1982 | Ochiai ............... A61K 8/19 424/49 |
| 5,376,360 | A | * | 12/1994 | Domke .............. A61K 8/19 424/49 |
| 7,195,753 | B1 | * | 3/2007 | Hall ................... A61K 8/40 424/49 |
| 8,580,234 | B2 | | 11/2013 | Isobe et al. |
| 2004/0120903 | A1 | | 6/2004 | Sagel et al. |
| 2005/0276760 | A1 | | 12/2005 | Lokken |
| 2008/0003248 | A1 | * | 1/2008 | Georgiades ....... A61K 8/0208 424/401 |
| 2011/0223119 | A1 | * | 9/2011 | Isobe ................. A61K 8/345 424/57 |
| 2014/0017180 | A1 | | 1/2014 | Isobe et al. |
| 2015/0289961 | A1 | | 10/2015 | Togo et al. |

FOREIGN PATENT DOCUMENTS

| CN | 102215813 A | 10/2011 |
| JP | 56-18913 A | 2/1981 |
| JP | 10-017447 A | 1/1998 |
| JP | 11-349460 A | 12/1999 |
| JP | 2003-335646 A | 11/2003 |
| JP | 2005-187330 A | 7/2005 |
| JP | 2008-081424 A | 4/2008 |
| JP | 2008-201732 A | 9/2008 |
| JP | 2010-111678 A | 5/2010 |
| WO | WO 2010/058522 A1 | 5/2010 |
| WO | WO 2012/137941 A1 | 10/2012 |
| WO | WO 2014/069595 A1 | 5/2014 |

OTHER PUBLICATIONS

ADA, "Fluoride treatments in the dental office", JADA, vol. 138, 420, Mar. 2007.*
International Search Report (ISR) for PCT/JP2013/079613; I.A. fd: Oct. 31, 2013, mailed Jan. 21, 2014, the Japanese Patent Office, Tokyo, Japan.
International Preliminary Report on Patentability (IPRP) including the Written Opinion of the International Searching Authority (PCT Rule 44bis) for PCT/JP2013/079613; I.A. fd: Oct. 31, 2013, issued May 5, 2015, by the International Bureau of WIPO, Geneva, Switzerland.
Excerpted prosecution history of U.S. Appl. No. 14/439,426, through Aug. 29, 2016.
Office action for CN 201380055572.3, Jul. 5, 2016, issued by SIPO, Beijing, China.
Excerpted prosecution history of U.S. Appl. No. 14/439,426: Applicant summary of interview (filed Sep. 29, 2016); Amendment and reply (filed Nov. 9, 2016); and non-final rejection (mailed Dec. 13, 2016).
Excerpted prosecution history of U.S. Appl. No. 14/439,426: Applicant's amendment and reply filed Apr. 12, 2017.

* cited by examiner

*Primary Examiner* — Jianfeng Song
(74) *Attorney, Agent, or Firm* — Sterne, Kessler, Goldstein & Fox P.L.L.C.

(57) ABSTRACT

Provided is a tooth whitener that is excellent in immediate effectivity of a gloss imparting effect on teeth and a tooth whitening effect. The tooth whitener is provided with a composition (A) and a composition (B) in a separate state, and which is to be used by applying the composition (A) and the composition (B) alternately to teeth.

17 Claims, No Drawings

TOOTH WHITENER

FIELD OF THE INVENTION

The present invention relates to a tooth whitener which is to be used by applying two kinds of compositions alternately to teeth.

BACKGROUND OF THE INVENTION

Human teeth are stained by adhesion of various staining substances on their surfaces as well as calculus and plaque, and the gloss of teeth also decreases. These staining and a decrease in gloss are not cosmetically desirable, and various means to whiten teeth are developed.

With such a background, for example, it has been known that phytic acid has activities such as removal of tobacco tar, a suppressive effect against calculus and stabilization of stannous fluoride, and a dentifrice containing phytic acid has been reported (Patent Document 1). In addition, an oral composition in which zeolite is blended (Patent Document 2), and a dentifrice composition in which particles having specific collapse strength (Patent Document 3) and the like are blended, in addition to phytic acid, have been also reported. Furthermore, the present applicant reported that conventional whiteners or abrasives cannot sufficiently remove minute solid matters with the height of less than 1 μm which adhered to a tooth surface, but use of a composition which contains phytic acid and no polyvalent cation and has pH adjusted to a certain range can remove minute solid matters which adhere to a tooth surface, and whiten the teeth and impart gloss to the teeth (Patent Document 4).

CITATION LIST

Patent Document

Patent Document 1: Japanese Patent Application No. 56-18913
Patent Document 2: JP 11-349460 A
Patent Document 3: JP 2003-335646 A
Patent Document 4: WO 2010/058522 A

SUMMARY OF THE INVENTION

The present invention relates to a tooth whitener which is provided with a composition (A) and a composition (B) in a separate state and which is to be used by applying the composition (A) and the composition (B) alternately to teeth, wherein:
the composition (A) comprises 0.1% by mass or more and 30% by mass or less of phytic acid or a salt thereof in terms of the acid, does not comprise any polyvalent metal cation, or alternatively comprises such cations in an amount of less than 0.1-fold mol relative to phytic acid or the salt thereof, exhibits a pH of 4 or more and 6.5 or less at 25° C., and comprises a fluoride in an amount such that the mass ratio of the fluoride in terms of fluorine atoms to the phytic acid in terms of the acid (the fluoride in terms of fluorine atoms/phytic acid) is 0.05 or less, or alternatively does not comprise any fluoride, and
the composition (B) comprises one or more selected from orthophosphoric acid, condensed phosphoric acid and salts thereof in an amount of 0.01% by mass or more and 15% by mass or less in terms of the acid and exhibits a pH of more than 6.5 and 10.5 or less at 25° C.

In addition, the present invention relates to a method of whitening teeth, which comprises applying a composition (A) and a composition (B) alternately to teeth, wherein:
the composition (A) comprises 0.1% by mass or more and 30% by mass or less of phytic acid or a salt thereof in terms of the acid, does not comprise any polyvalent metal cation, or alternatively comprises such cations in an amount of less than 0.1-fold mol relative to phytic acid or the salt thereof, exhibits a pH of 4 or more and 6.5 or less at 25° C., and comprises a fluoride in an amount such that the mass ratio of the fluoride in terms of fluorine atoms to the phytic acid in terms of the acid (the fluoride in terms of fluorine atoms/phytic acid) is 0.05 or less, or alternatively does not comprise any fluoride, and
the composition (B) comprises one or more selected from orthophosphoric acid, condensed phosphoric acid and salts thereof in an amount of 0.01% by mass or more and 15% by mass or less in terms of the acid and exhibits a pH of more than 6.5 and 10.5 or less at 25° C.

DETAILED DESCRIPTION OF THE INVENTION

Any above-mentioned composition has an effect of imparting gloss to teeth, but it is necessary to repeat the treatment to a certain extent. Therefore, it is desired to develop a technology for exerting enough tooth whitening effect while imparting gloss to teeth even with further shorter term use.

Accordingly, the present invention relates to a tooth whitener that is excellent in an immediate effectivity of gloss imparting effect on teeth and a tooth whitening effect.

Now, the present inventors further analyzed in detail components in a minute solid matter having a thickness of less than several μm adhered or deposited on the tooth surface, and found that not only calcium phosphates, but also organic matters are also contained. Furthermore, the present inventors found that use of a tooth whitener which is provided with a weak acidic specific composition containing phytic acid and a weak alkaline specific composition containing orthophosphoric acid or condensed phosphoric acid in a separate state, and which is to be used by applying these compositions alternately to teeth against a minute solid matter on the tooth surface derived from mixture of the organic matters and calcium phosphates, exerts an effect of further rapidly removing inorganic stains such as calcium phosphates and organic stains, and allows sufficiently obtaining a gloss imparting effect and an excellent whitening effect with short term use, and thus completed the invention.

According to the tooth whitener of the present invention, it is possible to rapidly remove minute stains or solid matters adhered or deposited on the tooth surface whereby to whiten teeth while imparting beautiful gloss to teeth even with short term use, and thus realize an immediately effective tooth-esthetic effect.

Hereinafter, the invention will be explained in detail.

Furthermore, the minute stains or solid matters adhered or deposited on the tooth surface in the present invention refer to a solid matter having a thickness of less than several μm and adhered and deposited on the tooth surface, and such solid matter includes aggregates containing inorganic matters as a main component and aggregates containing organic matters as a main component, and also includes those having a structure in which each aggregate is layered or sea-island-shaped. This minute solid matter is considered to be mainly formed by adhesion of components such as a protein, calcium and phosphorus in the saliva and formed by deposition of adhered matters. The minute sold matter is easily produced by promotion of the adhesion or deposition by deterioration of the environment in the oral cavity due to aging or a decrease of saliva secretion, and the like, and is difficult to be removed with an ordinary brushing treatment. According to the tooth whitener of the present invention, it is possible to suitably act on aged yellow teeth which lack gloss, and improve the whiteness and the gloss in a short term.

The tooth whitener of the present invention is provided with the composition (A) and the composition (B) in a separate state, and is to be used by applying these compositions alternately to teeth. Once the composition (A) and the composition (B) are applied alternately to teeth, then further successively the composition (A) and the composition (B) can be applied alternately to teeth, which can be repeated many times. The tooth whitener of the present invention exerts the immediately effective esthetic-tooth effect, and thus can make the tooth whitened and glossy with only short term use, for example, repetition of application of the composition (A) and the composition (B) alternately to teeth multiple times. The order of applying these compositions to teeth is not particularly limited, and the composition (A) may be first applied to teeth, and then the composition (B) may be applied to the teeth, or the composition (B) may be first applied to teeth, and then the composition (A) may be applied to the teeth. It is preferred from the point of obtaining the effects in a further short term that the composition (B) is first applied to teeth, and then the composition (A) is applied to the teeth. In addition, the application times of the composition (A) and the composition (B) are preferably such that the application time of the composition (A) is longer than the application time of the composition (B) from the point of obtaining the effects in a further short term. In addition, when the composition (A) and the composition (B) are applied alternately to teeth, it is preferred that after one composition is applied, the other composition is rapidly applied. The time from completion of the application of one composition to initiation of the application of the other composition is preferably 3 minutes or less, more preferably 1 minute or less, even more preferably 30 seconds or less.

Furthermore, the phrase that the composition (A) and the composition (B) are provided in a separate state in the tooth whitener of the present invention means that these compositions are not mixed before application to teeth, and these compositions are present in a separated embodiment so that each composition can be applied in order to the teeth. Consequently, for example as described below, when these compositions are together a dentifrice composition such as a toothpaste or a liquid oral composition such as a mouthwash, it includes an embodiment in which the compositions are filled into individual containers in an isolated state from each other. Alternatively, when these compositions are sheets, it includes an embodiment in which each sheet is multiple-layered and adhered tightly each other to form one sheet. In addition, the sheet in the present invention refers to an agent that is provided with a single layer or multiple layers including the composition (A) and/or the composition (B) used in the tooth whitener of the present invention, is in a flexible, a thin-plate form, is used by being directly attached on the tooth surface, and has a property of being dissolved or a property of eluting active components in the saliva in the oral cavity after the attachment.

The composition (A) provided in the tooth whitener of the present invention contains 0.1% by mass or more and 30% by mass or less of phytic acid or a salt thereof in terms of the acid. Phytic acid or a salt thereof has an excellent tooth whitening action and a gloss imparting action, the whitening action and gloss imparting action thereof are remarkably enhanced by applying the composition (A) to teeth while alternating with the composition (B) containing orthophosphoric acid, condensed phosphoric acid or salts thereof described below, and the excellent tooth whitening effect and the gloss imparting effect can be provided even with short term use. Phytic acid is also referred to as myo-inositol hexaphosphoric acid as another name, and is an inositol phosphoric acid ester compound. Phytic acid or a salt thereof has particularly the excellent gloss imparting effect among various phosphoric acid compounds.

Examples of the salt thereof include alkali metal salts such as sodium and potassium, ammonium salts and the like, and the salt thereof is preferably one or more selected from them, and is preferably an alkali metal salt from the viewpoint of the taste and the smell.

The content of phytic acid or a salt thereof in the composition (A) is 0.1% by mass or more, preferably 0.2% by mass or more, more preferably 0.3% by mass or more in terms of the acid in the composition (A) from the viewpoint of sufficiently exerting the gloss imparting effect and the whitening effect by the minute solid matter-removing effect. The content of phytic acid or a salt thereof in the composition (A) is 30% by mass or less, preferably 20% by mass or less in terms of the acid in the composition (A) from the viewpoint of further smoothing the tooth surfaces and improving the gloss and from the viewpoint of taste and friction. Furthermore, when the composition (A) has a form of a sheet, that is attached to teeth and then is slowly dissolved and diluted to be applied, the content of phytic acid or a salt thereof is preferably 26% by mass or less, more preferably 20% by mass or less, even more preferably 16% by mass or less in terms of the acid in the composition (A). Alternatively, when the composition (A) has a form of a dentifrice composition such as a toothpaste, or a liquid oral composition such as a mouthwash, the content of phytic acid or a salt thereof is preferably 15% by mass or less, more preferably 5% by mass or less, even more preferably 3% by mass or less, even more preferably 1.5% by mass or less in terms of the acid from the viewpoint of a feeling upon use. When the composition (A) has a form of a sheet that is attached to teeth and then is slowly dissolved and diluted to be applied, the content of phytic acid or a salt thereof is preferably 2% by mass or more, more preferably 5% by mass or more, even more preferably 12% by mass or more in terms of the acid in the composition (A). Thus, the content of phytic acid or a salt thereof in the composition (A) is 0.1% by mass or more and 30% by mass or less, preferably from 0.2 to 20% by mass in terms of the acid in the composition (A). When the composition (A) is a sheet, the content of phytic acid or a salt thereof in the composition (A) is preferably from 0.2 to 26% by mass, more preferably from 5 to 26% by mass, even more preferably from 5 to 20% by mass, even more preferably from 12 to 16% by mass in terms of the acid. When the composition (A) is a dentifrice composition or a liquid oral composition, the content of phytic acid or a salt thereof in the composition (A) is preferably from 0.1 to 15% by mass, more preferably from 0.2 to 5% by mass, even more preferably from 0.2 to 3% by mass, even more preferably from 0.2 to 1.5% by mass in terms of the acid.

Furthermore, the content of phytic acid or a salt thereof in the composition (A) is a value obtained by measuring the total amount by neutralization using potassium hydroxide or sodium hydroxide, and converting it to the acid amount. In addition, the content of phytic acid or a salt thereof in the composition (A) when the composition (A) is a sheet means a value by dry mass.

In the composition (A), the content of the polyvalent metal cation is suppressed. The polyvalent metal cation renders phytic acid to be insoluble or decreases the effect of removing the solid matter. Therefore, the content of the polyvalent metal cation is suppressed to prevent a decrease of the effects. The content thereof is measured by ICP emission spectrometry (ICP emission spectrometer: Optima 5300DV manufactured by PerkinElmer Inc.), and the total content of the polyvalent metal cation is less than 0.1-fold mol, preferably 0.02-fold mol or less, more preferably 0.01-fold mol or less relative to phytic acid or a salt thereof. That is, it is desired that agents for mainly supplying polyvalent metal cations such as aluminum, calcium, magnesium, iron, zinc and tin are not blended, or the polyvalent metal cation may not be contained except the case of inevitable contamination.

In addition, absorbents such as zeolite and activated carbon in addition to the cationic antibacterial agent that is a polyvalent cation other than the polyvalent metal cation reduces the solid matter-removing effect by phytic acid or a salt thereof, and thus the content thereof is preferably less than 0.001% by mass, more preferably 0.0001% by mass or less in the composition (A), and the composition (A) preferably does not contain the absorbents and agents except the case of inevitable contamination.

The composition (A) exhibits a pH of 4 or more and 6.5 or less. By adjusting the pH of the composition (A) to such weak acidic range, when the composition is applied into the oral cavity, the composition can particularly effectively act on inorganic stains to remove the minute solid matter, and suppress decalcification of tooth surfaces to sufficiently exert the immediately effective gloss imparting effect and the whitening effect on the enamel surface and into the interprismatic space of the enamel. The pH of the composition (A) is 4 or more, preferably 4.5 or more from the viewpoint of showing the immediately effective gloss imparting effect and the whitening effect. When the composition (A) is a dentifrice composition or a liquid oral composition, the pH of the composition (A) is more preferably 4.8 or more, even more preferably 5 or more. The pH of the composition (A) is 6.5 or less, preferably 6.2 or less from the viewpoint of sufficiently showing the gloss imparting effect and the whitening effect by removing the solid matter. In addition, the composition (A) exhibits a pH of from 4 to 6.5, preferably from 4.5 to 6.2, more preferably from 4.8 to 6.2. When the composition (A) is a dentifrice composition or a liquid oral composition, the pH is even more preferably from 5 to 6.2.

In addition, the composition (A) may contain one or more fluorides selected from fluoride ion-supplying compounds such as sodium fluoride, potassium fluoride, ammonium fluoride and stannous fluoride, and sodium monofluorophosphate that is a fluoride other than these fluoride ion-supplying compounds and the like in a range in which the gloss imparting effect of phytic acid or a salt thereof is not inhibited (the content, the dosage form and the like). The composition (A) may contain these fluorides in an amount such that the mass ratio of the fluoride in terms of fluorine atoms to the phytic acid or a salt thereof in terms of the acid (the fluoride in terms of fluorine atoms/phytic acid) is 0.05 or less, preferably 0.03 or less, more preferably 0.01 or less, even more preferably 0.005 or less, even more preferably 0.001 or less, or may not contain any fluoride except the case of inevitable contamination from the viewpoint of further enhancing the gloss imparting effect and the whitening effect of phytic acid or a salt thereof.

Furthermore, the fluoride is preferably one or more selected from sodium fluoride, potassium fluoride, ammonium fluoride, stannous fluoride and sodium monofluorophosphate, and the amount of the fluoride in terms of fluorine atoms when two or more fluoride compounds are contained means the amount in terms of fluorine atoms that is calculated from the total content of these fluorides. In addition, the content of the fluoride in the composition (A), when the composition (A) is a sheet, means a value by dry mass.

The pH of the composition (A) is measured at 25° C. The pH of the composition (A) cannot be exactly measured, for example, when the composition (A) is a composition having high viscosity such as a dentifrice composition such as a toothpaste, or when the composition (A) is made into a sheet. Thus, when the composition (A) is a composition having high viscosity such as a dentifrice composition such as a toothpaste, the composition is diluted to reach 30% by mass with water, followed by measurement, which is assumed as the pH of the composition (A). In addition, when the composition (A) is made into a sheet, the surface of the sheet including the composition (A) is inclined by 45 degrees with respect to the horizontal surface, water in such an amount that does not dissolve the sheet and make a hole, for example, 0.1 to 0.5 g, is dropped onto the surface of the sheet, then the dropped water is rapidly collected by using the inclination of 45 degrees, and the pH is measured by using, for example, compact pH meter-712 (HORIBA, Ltd.). The value obtained by such measurement method is assumed as the pH of the composition (A) based on a situation in which the tooth whitener of the present invention is applied into the oral cavity and the composition (A) acts. When the composition (A) is a dentifrice composition such as a toothpaste, the pH of the composition (A) is obtained in consideration of dilution in the oral cavity, and when the composition (A) is a sheet, the pH of the composition (A) is obtained in consideration that the sheet is attached to teeth, slowly dissolved and diluted.

Furthermore, when the composition (A) is a sheet, the value of the pH of a base material solution prepared before formation of the sheet is roughly the same as the value of the pH obtained by dropping purified water to the sheet and measuring the pH of the dropped water as described above. Thus, the pH of the base material solution prepared before formation of the sheet is assumed as the pH of the composition (A). In addition, when the composition (A) is a liquid oral composition having low viscosity such as a mouthwash and a liquid dentifrice, the value of the pH obtained by measuring the base material solution is assumed as the pH of the composition (A). In any case, water is purified water and distilled water or ion exchanged water is used.

A pH regulator is preferably used to adjust the pH of the composition (A) to the above-described range. Examples of the pH regulator include salts of organic acid such as acetic acid, fumaric acid, malic acid, lactic acid, gluconic acid and tartaric acid; salts of inorganic acid such as condensed phosphoric acid, phosphoric acid other than phytic acid and condensed phosphoric acid, hydrochloric acid and sulfuric acid; hydroxides such as sodium hydroxide; ammonia or ammonia water, lower alkanolamines, basic amino acids such as arginine and lysine; and the like as long as the gloss imparting effect and the whitening effect of phytic acid or a salt thereof are not inhibited and decalcification of teeth can be suppressed. These may be used individually, or two or more may be used in combination. The content of the organic acid and the inorganic acid (except phytic acid) among these pH regulators is preferably 5 mass parts or less, more preferably 1 mass part or less relative to 100 mass parts of the phytic acid or a salt thereof in terms of the acid from the viewpoint of not inhibiting the whitening effect and the gloss imparting effect of phytic acid or a salt thereof. When a condensed phosphoric acid salt such as an alkali metal salt of condensed phosphoric acid is used as the pH regulator of the composition (A), the content of the condensed phosphoric acid salt is preferably equivalent mole or less, more preferably 0.5 mole or less with respect to the phytic acid or a salt thereof from the viewpoint of not inhibiting the gloss imparting effect of phytic acid or a salt thereof. The mass ratio to the phytic acid or a salt thereof in terms of the acid (condensed phosphoric acid salt/phytic acid) is preferably 0.5 or less, more preferably 0.2 or less, even more preferably 0.1 or less.

The composition (B) provided in the tooth whitener of the present invention contains one or more selected from orthophosphoric acid, condensed phosphoric acid and salts thereof in an amount of 0.01% by mass or more and 15% by mass or less in terms of the acid. Orthophosphoric acid, condensed phosphoric acid and salts thereof are effective as a gloss enhancing agent for enhancing the gloss imparting action of phytic acid or a salt thereof, and can enhance the tooth whitening action and the gloss imparting action of phytic acid or a salt thereof and sufficiently enhance the effects thereof even with short term use by being applied to teeth alternately with the composition (A). Examples of the condensed phosphoric acid include pyrophosphoric acid, tripolyphosphoric acid, tetrapolyphosphoric acid and metaphosphoric acid. In addition, the salts of orthophosphoric acid and condensed phosphoric acid are preferably alkali metal salts such as sodium salts and potassium salts, specifically, for example, sodium pyrophosphate, potassium pyrophosphate, sodium tripolyphosphate and potassium tripolyphosphate. Among them, pyrophosphoric acid, tripolyphosphoric acid or an alkali metal salt thereof is preferable, and sodium pyrophosphate is more preferable from the viewpoint of enhancing the tooth whitening action and the gloss imparting action with short term use. Furthermore, one or more selected from orthophosphoric acid, various condensed phosphoric acid and salts thereof described above can be used in the composition (B).

The content of the one or more selected from orthophosphoric acid, condensed phosphoric acid and salts thereof in the composition (B) is 0.01% by mass or more, preferably 0.02% by mass or more, more preferably 0.1% by mass or more, even more preferably 0.5% by mass or more in terms of the acid in the composition (B) from the viewpoint of sufficiently exerting the minute solid matter-removing effect, and the gloss imparting effect and the whitening effect of phytic acid or a salt thereof. When the composition (B) is a sheet, the content of the one or more selected from orthophosphoric acid, condensed phosphoric acid and salts thereof in the composition (B) is preferably 1% by mass or more, more preferably 3% by mass or more, even more preferably 5% by mass or more in terms of the acid. The content of the one or more selected from orthophosphoric acid, condensed phosphoric acid and salts thereof in the composition (B) is 15% by mass or less in terms of the acid in the composition (B) from the viewpoint of taste and a feeling upon use such as friction, and from the viewpoint of promoting the whitening effect and the gloss imparting effect of phytic acid or a salt thereof. When the composition (B) is a sheet, the content of the one or more selected from orthophosphoric acid, condensed phosphoric acid and salts thereof in the composition (B) is preferably 12% by mass or less, more preferably 10% by mass or less, even more preferably 7% by mass or less in terms of the acid. When the composition (B) is a dentifrice composition such as a toothpaste, or a liquid oral composition such as a mouthwash, the content of the one or more selected from orthophosphoric acid, condensed phosphoric acid and salts thereof in the composition (B) is preferably 7% by mass or less, more preferably 5% by mass or less, even more preferably 3% by mass or less, even more preferably 1% by mass or less in terms of the acid from the viewpoint of a feeling upon use and taste. In addition, the content of the one or more selected from orthophosphoric acid, condensed phosphoric acid and salts thereof in the composition (B) is 0.01% by mass more and 15% by mass or less, preferably from 0.02 to 12% by mass, more preferably from 0.1 to 10% by mass in terms of the acid. Furthermore, when the composition (B) is a sheet, the content of the one or more selected from orthophosphoric acid, condensed phosphoric acid and salts thereof is preferably from 1 to 15% by mass, more preferably from 3 to 12% by mass, even more preferably from 5 to 12% by mass, even more preferably from 5 to 7% by mass in terms of the acid. In addition, when the composition (B) is a dentifrice composition such as a toothpaste, or a liquid oral composition such as a mouthwash, the content of the one or more selected from orthophosphoric acid, condensed phosphoric acid and salts thereof is preferably from 0.02 to 7% by mass, more preferably from 0.02 to 5% by mass, even more preferably from 0.02 to 3% by mass, even more preferably from 0.1 to 3% by mass, even more preferably from 0.1 to 1% by mass, even more preferably from 0.5 to 1% by mass in terms of the acid.

Furthermore, the content of the one or more selected from orthophosphoric acid, condensed phosphoric acid and salts thereof in the composition (B) is a value obtained by measuring the total amount by neutralization using potassium hydroxide or sodium hydroxide, and converting it to the acid amount. In addition, when the composition (B) is a sheet, the content of the one o or more selected from orthophosphoric acid, condensed phosphoric acid and salts thereof in the composition (B) means a value by dry mass.

The composition (B) exhibits a pH of more than 6.5 and 10.5 or less. By adjusting the pH of the composition (B) to such alkaline range than the composition (A), when the composition (B) is applied into the oral cavity the composition can effectively act on particularly organic matter stains that are strongly sedimented or deposited near tooth surfaces whereby to remove minute solid matters, suppress decalcification of tooth surfaces, and exert the whitening effect and the gloss imparting effect of phytic acid or a salt thereof immediately effectively and sufficiently. For these reasons, the composition (B) is considered to function as a component promoting the effects of the composition (A) in the present invention. The pH of the composition (B) is more than 6.5, preferably 7.0 or more, more preferably 7.5 or more, even more preferably 8 or more from the viewpoint of showing the immediately effective gloss imparting effect and the whitening effect of the composition (A). The pH of the composition (B) is 10.5 or less, preferably 10 or less, more preferably 9.5 or less, even more preferably 9 or less from the viewpoint of sufficiently showing the gloss imparting effect and the whitening effect of the composition (A). In addition, the pH of the composition (B) is more than 6.5 and 10.5 or less, preferably from 7.0 to 10, more preferably from 7.5 to 9.5, even more preferably from 8 to 9.

The pH of the composition (B) is measured at 25° C., and is a value obtained by a measurement method similar to that for the pH of the composition (A). In addition, water is also purified water and distilled water or ion exchanged water is used. Furthermore, a pH regulator is preferably used in order to adjust the pH of the composition (B). Examples of the pH regulator include salts of organic acid such as acetic acid, fumaric acid, malic acid, lactic acid, gluconic acid and tartaric acid; phytic acid or phosphoric acid other than orthophosphoric acid and condensed phosphoric acid or a salt thereof; salts of inorganic acid such as hydrochloric acid and sulfuric acid; hydroxides such as sodium hydroxide; ammonia or ammonia water, lower alkanolamines, basic amino acids such as arginine and lysine; and the like as long as the minute solid matter-removing effect is not inhibited and decalcification of teeth can be suppressed. These may be used individually, or two or more may be used in combination. Among these pH regulators, the content of the organic acid and the inorganic acid (except orthophosphoric acid and condensed phosphoric acid) is preferably 5 mass parts or less, more preferably 1 mass part or less relative to 100 mass parts of orthophosphoric acid, condensed phosphoric acid and salts thereof in terms of the acid from the viewpoint of not inhibiting the minute solid matter-removing effect. When phytic acid is used as the pH regulator of the composition (B), the mass ratio of phytic acid or a salt thereof in terms of the acid to orthophosphoric acid, condensed phosphoric acid and salts thereof in terms of the acid (phytic acid/orthophosphoric acid and condensed phosphoric acid) is preferably 0.3 or less, more preferably 0.2 or less, even more preferably 0.1 or less.

The composition (B) may further contain a fluoride. By containing such fluoride, it is possible to achieve good resistance to dissolution in acid and recalcification, and thus achieve the immediately effective gloss imparting effect and the whitening effect as well as strengthening of teeth. Furthermore, the fluoride is preferably contained in the composition (A) as long as the gloss imparting effect of phytic acid or a salt thereof is not inhibited, while is desirably contained in the composition (B) to sufficiently exert the effects of the fluoride.

Such fluoride is as described above and examples thereof include fluoride ion-supplying compounds such as sodium fluoride, potassium fluoride, ammonium fluoride and stannous fluoride, and sodium monofluorophosphate that is a fluoride other than these fluoride ion-supplying compounds. The content of the fluoride in the composition (B) is preferably 0.001% by mass or more, more preferably 0.005% by mass or more in the composition (B) in terms of fluorine atoms from the viewpoint of increasing the amount of incorporated fluorine. The content of the fluoride in the composition (B) is preferably 0.2% by mass or less, more preferably 0.15% by mass or less, even more preferably 0.1% by mass or less in the composition (B) in terms of fluorine atoms from the viewpoint of not inhibiting the effects of the composition (A) which is applied to teeth alternately with the composition (B). In addition, the content of the fluoride compound in the composition (B) is preferably from 0.001 to 0.2% by mass, more preferably from 0.005 to 0.15% by mass, even more preferably from 0.005 to 0.1% by mass in terms of fluorine atoms.

Furthermore, when the composition (B) is a sheet, the content of the fluoride in the composition (B) means a value by dry mass.

Furthermore, when the composition (B) contains a fluoride, it is preferred that the composition (B) is first applied to teeth, and then the composition (A) is applied to the tooth from the viewpoint of not inhibiting the effects of the composition (A) which is applied to teeth alternately with the composition (B), which may be repeated successively with the compositions applied alternately to teeth.

The tooth whitener of the present invention may be further provided with a composition (C) containing a fluoride in a separate state in addition to the composition (A) and the composition (B). At this time, it is preferred that the composition (A) and the composition (B) are applied to the teeth, followed by application of the composition (C). From the viewpoint of further enhancing the effect of the composition (C), it is preferred that the composition (A) is applied and then the composition (B) is applied, followed by application of the composition (C). From the viewpoint of enhancing the effects of the composition (A), it is preferred that the composition (B) is applied and then the composition (A) is applied, followed by application of the composition (C). In addition, this may be repeated successively with the compositions applied alternately to teeth. By this, it is possible to make the composition (A) firstly act prior to the composition (C), and effectively reduce inhibition of the effects of the composition (A) by the fluoride.

The content of the fluoride in the composition (C) is preferably 0.001% by mass or more, more preferably 0.005% by mass or more in the composition (C) in terms of fluorine atoms from the viewpoint of increasing the amount of incorporated fluorine. The content of the fluoride in the composition (C) is preferably 0.02% by mass or less, more preferably 0.015% by mass or less, even more preferably 0.01% by mass or less in the composition (C) in terms of fluorine atoms from the viewpoint of not inhibiting the effects of the composition (A) and being effectively applied to teeth. In addition, the content of the fluoride in the composition (C) is preferably from 0.001 to 0.2% by mass, more preferably from 0.005 to 0.15% by mass, even more preferably from 0.005 to 0.1% by mass in the composition (C) in terms of fluorine atoms.

Furthermore, when the composition (C) is a sheet as described below, the content of the fluoride in the composition (C) means a value by dry mass.

In addition to the above components, for example, a foaming agent, a foam booster, an abrasive, a humectant, a thickening agent, a gelling agent, a binder, a sweetening agent, a preservative, an antibacterial agent, a medicinally active ingredient, a pigment, a colorant, a flavor and the like may be properly contained, or polyethylene glycol, which is a conventionally used whitening component, and the like may be also blended in the composition (A) and the composition (B), or the composition (C) that is used as necessary.

The composition (A) and the composition (B), or the composition (C) that is used as necessary may be produced to a dosage form of a solution, a gel and a paste, and made into a form of a dentifrice composition such as a wet dentifrice (a gel dentifrice) and a toothpaste, a composition for application such as a gel and an ointment adhered to teeth, or a liquid oral composition such as a liquid dentifrice and a mouthwash. In addition, these compositions may be made into an application material such as cloth and fiber impregnated with the composition, made into a dental hygiene device such as dental floss impregnated with these compositions, or made into food such as chewing gum, troche and candy. Furthermore, sheets containing these compositions may be formed, and an integrated sheet in which each sheet is laminated, may be formed. Furthermore, the forms of these compositions may be the same or different from each other. For example, the composition (A) may be a dentifrice, and the composition (B) may be a liquid dentifrice or a mouthwash, and vice versa. From the viewpoint of long time application, it is preferred that at least the composition (A) is a sheet; it is more preferred that both of the composition (A) and the composition (B) are sheets; and it is further preferred that both of the sheet of composition (A) and the sheet of composition (B) are laminated as sheet layers to form one integrated sheet (laminated sheet). In addition, from the viewpoint of ease of use, it is preferred that both or either one of the composition (A) and the composition (B) is a mouthwash or toothpaste.

Any dosage form may contain polyethylene glycol, propylene glycol, glycerin, sorbitol, maltitol, xylitol, lactitol or the like for the purpose of a humectant or a thickening agent or the like.

In addition, one or more selected from sodium carboxymethylcellulose, hydroxymethylcellulose, hydroxyethylcellulose, hydroxypropylcellulose, hydroxypropylmethylcellulose, a carboxyvinyl polymer, xanthan gum, carrageenan, sodium alginate, pullulan, guar gum, sodium chondroitin sulfate and the like can be contained as a thickening agent of a liquid oral composition, as a gelling agent of a gel composition, or as a binder of a dentifrice composition (a paste composition), further as a gelling agent in formation of a sheet using the liquid composition. Among these, a cellulose-based binder such as sodium carboxymethylcellulose, hydroxyethylcellulose, hydroxymethylcellulose and hydroxypropylmethylcellulose, or a non-cellulose-based binder such as xanthan gum, pullulan and guar gum is preferably contained in the composition (A) from the viewpoint of sufficiently exerting the gloss imparting effect of phytic acid or a salt thereof and from the viewpoint of a feeling upon use and stability, and a the cellulose-based binder and the non-cellulose-based binder are preferably contained in combination.

In addition, when the salt concentration is high, for example, due to a buffer solution, it is preferred that one or more selected from non-ionic polymers, that is, hydroxyethylcellulose, guar gum, hydroxypropylcellulose, hydroxypropylmethylcellulose, pullulan and the like is contained.

When any one of the composition (A) and the composition (B), or the composition (C) that is used as necessary is a dentifrice composition, the viscosity at 25° C. is preferably 500 to 10000 dPa·s, more preferably 1000 to 7000 dPa·s, even more preferably 1200 to 5000 dPa·s from the viewpoint of a sufficient gloss imparting effect. Here, the viscosity can be measured using a helical path viscometer (VISCOMETER TVB-10 manufactured by Toki Sangyo Co., Ltd) at a measuring temperature of 25° C. under measuring conditions of T-C spindle and 2.5 r/min of the number of revolutions for 1 minute.

When any one of the composition (A) and the composition (B), or the composition (C) that is used as necessary is a dentifrice composition, for example, a toothpaste, the composition may contain granules. However, from the viewpoint of effectively acting on organic stains strongly sedimented or deposited near tooth surfaces to remove minute solid matters and promoting gloss formation, it is preferred that granules not be blended, or granules with the collapse strength of 10 g/granule or less in a dry state, and preferably granules with the collapse strength of 10 g/granule or less in the coexistence of water be contained, and preferably substantially not contained. In addition, an abrasive may be contained as long as the gloss formation effect of the present invention is not inhibited, and for example, a silica abrasive such as hydrous silica, anhydrous silica and silica gel is preferably used.

Furthermore, when any one of the composition (A) and the composition (B), or the composition (C) that is used as necessary is a sheet, the content of each of the components in each of these compositions is properly selected based on a value by dry mass.

The application to teeth of the composition (A) and the composition (B), or the composition (C) provided as necessary, which are provided in the tooth whitener of the present invention, includes both direct application and application in a diluted state with water, saliva, or the like. In addition, a liquid oral composition such as a mouthwash is applied to teeth without dilution, and a sheet obtained by forming sheet layers from the liquid composition and laminating the same is directly attached on the tooth surfaces and the sheet is dissolved whereby to be applied. On the other hand, when the composition is a dentifrice composition or the like, the dentifrice composition is generally applied with dilution to about 4-fold by mass with saliva in application using a toothbrush and the like.

It is preferred that either one or both of the composition (A) and the composition (B) provided in the tooth whitener of the present invention is a sheet, and it is preferred that at least the composition (A) is a sheet from the viewpoint of effectively obtaining the tooth whitening action and the gloss imparting action within a further short term. When the composition (A) is a sheet, the thickness of the sheet of the composition (A) is preferably 200 µm or less, more preferably 100 µm or less, even more preferably 60 µm or less from the viewpoint of dissolving the sheet within a suitable time and obtaining suitable flexibility as a sheet, and is preferably 10 µm or more, more preferably 15 µm or more, even more preferably 20 µm or more from the viewpoint of obtaining the tooth whitening action and the gloss imparting action with short term use, and from the viewpoint of ease of use and manufacturability. When the composition (B) is a sheet, the thickness of the sheet of the composition (B) is preferably 100 µm or less, more preferably 50 µm or less, even more preferably 20 µm or less, and is preferably 1 µm or more, more preferably 5 µm or more, even more preferably 7 µm or more from the viewpoint of dissolving the sheet within a suitable time and securing suitable flexibility as the sheet.

Furthermore, when the composition (C) is a sheet, the thickness of the sheet of the composition (C) is preferably 100 µm or less, more preferably 50 µm or less, even more preferably 20 µm or less, and is preferably 1 µm or more, more preferably 5 µm or more, even more preferably 7 µm or more from the viewpoint of dissolving the sheet within a suitable time and obtaining suitable flexibility as the sheet.

When both of the composition (A) and the composition (B) provided in the tooth whitener of the present invention are sheets, it is preferred that the sheet constituting the side attached to teeth is the sheet of the composition (A) when the sheet is attached to teeth from the viewpoint of first allowing phytic acid or a salt thereof to sufficiently act under the environment of pH 4 or more and 6.5 or less, and then allowing orthophosphoric acid, condensed phosphoric acid or salts thereof to sufficiently act under the environment of pH more than 6.5 and 10.5 or less. In addition, when the adhesive sheet of the present invention is attached to teeth, it is preferred that the sheet constituting the side attached to teeth is the sheet of the composition (B) from the viewpoint of first allowing orthophosphoric acid, condensed phosphoric acid or salts thereof to sufficiently act under the environment of pH more than 6.5 and 10.5 or less, and then allowing phytic acid or a salt thereof to sufficiently act under the environment of pH 4 or more and 6.5 or less.

Furthermore, in this case, the thickness ratio of the sheet of the composition (B) to the sheet of the composition (A) ($B_t/A_t$) is preferably from 1/10 to 1/1, more preferably from 1/9 to 1/2, even more preferably from 1/8 to 1/3.

In addition, when the composition (A) and the composition (B), the composition (C) as necessary are made into sheets, and one sheet (laminated sheet) is obtained by laminating these sheets as sheet layers whereby to be integrated, it is preferred that a water-insoluble coating sheet (X) is further laminated and arranged on the surface of the opposite side to the layer attached to teeth so that the side attached to teeth is first dissolved with saliva and applied to teeth. By arranging the coating sheet (X), it is possible to effectively prevent the composition constituting the layer of the opposite side to the layer attached to teeth from being dissolved with saliva and the like when the tooth whitener is attached to teeth. The above-mentioned water-insoluble coating sheet (X) is a sheet remaining without dissolution or decomposition while covering teeth even after the composition (A), the composition (B) and the composition (C) provided as necessary are dissolved or decomposed, or a sheet that is not dissolved or decomposed although the water-insoluble coating sheet (X) may be a component that is dissolved with or decomposed by saliva. The coating sheet (X) is thicker than the thickness of the composition (A), the composition (B) and the composition (C) provided as necessary, or is different in the components such as a polymer constituting the sheet. Examples of the component of the coating sheet (X) include one or more polymers or copolymers selected from cellulose acetate phthalate, polyvinyl acetate, ethylcellulose, polymethylmethacrylate, a methacryloylethylbetaine-methacrylate copolymer, a methacrylic acid copolymer and an aminoalkyl methacrylate copolymer. The component of the coating sheet (X) is preferably ethylcellulose or cellulose acetate phthalate from the viewpoint of enhancing adhesion of the composition (A), the composition (B), and the composition (C) as necessary, and from the viewpoint of easy availability. Furthermore, the content of the polymer or the copolymer such as ethylcellulose and cellulose acetate phthalate in such coating sheet (X) is preferably from 40 to 95% by mass, more preferably from 50 to 90% by mass based on dry mass. The thickness of the coating sheet (X) is preferably 40 µm or less, and 0.5 µm or more, 1 µm or more from the viewpoint of securing suitable flexibility as a sheet.

Furthermore, when multiple sheets are selected as a sheet layer from among the composition (A), the composition (B), the composition (C) and the coating sheet (X) and laminated to one sheet (laminated sheet), a middle sheet (Y) may be arranged as a middle layer between the sheets. Such middle sheet (Y) may be formed between any of the sheets. For example, by having the middle sheet (Y) between the sheet of the composition (A) and the sheet of the composition (B), these compositions are easily formed in a separate state without mixture of the composition (A) and the composition (B) at the time of manufacture, and pH stabilities of the composition (A) and the composition (B) are easily improved at the time of storage. In addition, it becomes easy at the time of use that one sheet is dissolved and the contained components are released into the oral cavity, and then subsequently the other sheet is dissolved and the contained components are released into the oral cavity.

The material for the middle sheet (Y) is preferably non-ionic polymers such as pullulan, hydroxyethylcellulose, guar gum, hydroxypropylcellulose and hydroxypropylmethylcellulose, or the like from the viewpoint of enhancing followability to the other sheets. For example, when the middle sheet (Y) is formed between the sheet of the composition (A) and the sheet of the composition (B), the material for the middle sheet (Y) is preferably one or more (co)polymers selected from cellulose acetate phthalate, polyvinyl acetate, ethylcellulose, polymethylmethacrylate, a methacryloylethylbetaine-methacrylate copolymer, a methacrylic acid copolymer and an aminoalkyl methacrylate copolymer from the viewpoint of enhancing separation of these compositions.

The thickness of the middle sheet (Y) is preferably 1 µm or more, more preferably 5 µm or more, even more preferably 10 µm or more from the viewpoint of effectively preventing first dissolution of the layer of the opposite side to the side attached to teeth whereby preferentially dissolving the layer of the side attached to teeth. The thickness of the middle sheet is preferably 100 µm or less, more preferably 50 µm or less, even more preferably 30 µm or less from the viewpoint of ease use for a user.

The middle sheet (Y) preferably exhibits a pH of from 6.5 to 7.0.

When the composition (A), the composition (B) and the composition (C) as necessary are made into sheets (sheet layer) and a water-insoluble sheet (sheet layer) and a middle sheet (middle layer) are arranged, it is preferred that a plasticizer is contained as necessary from the viewpoint of imparting suitable stiffness and flexibility to any of the sheets and from the viewpoint of securing good formability. Such plasticizer is preferably one or more selected from phthalic acid ester, adipic acid ester, trimellitic acid ester, citric acid ester and fatty acid ester.

When multiple sheets are selected as sheet layers from among, for example, the composition (A), the composition (B), the composition (C), the coating sheet (X) and the middle sheet (Y), and they are laminated to obtain one sheet (laminated sheet) as described above, the total thickness of the sheet is preferably 10 µm or more, more preferably 20 µm or more, even more preferably 30 µm or more, and is preferably 1000 µm or less, more preferably 500 µm or less, even more preferably 100 µm or less from the viewpoint of enhancing followability to teeth when the sheet is attached, and from the viewpoint of realizing the immediately effective gloss imparting effect and the whitening effect.

<Method of Producing Sheet>

A method of producing the sheet includes a step of preparing a base material solution which further contains water in addition to the composition (A), and/or a base material solution which further contains water in addition to the composition (B), a step of applying these base material solutions on a substrate such as a polyethylene terephthalate (PET) film subjected to mould release treatment and the like in consideration of the basis weight and the thickness, and a step of further drying the substrate. Thus, by detaching the base such as a PET film, it is possible to obtain a sheet. When both of the composition (A) and the composition (B) are made into sheets (sheet layer), and these are laminated to give one sheet (laminated sheet), the method of producing the sheet preferably includes a step of forming two sheets, respectively, laminating them, and then pressing them using, for example, a heated pressure device whereby forming a bi-layered constitution.

When the composition (C) is made into a sheet, the method of producing the sheet is similar to the method described above except that the method includes a step of preparing a base material solution which further contains water in addition to the composition (C). In addition, when a further water-insoluble sheet is arranged, the method of producing the sheet may include a step of applying any one of the base material solutions mentioned above on such water-insoluble sheet as a substrate, or may include a step of forming a sheet of the above-mentioned composition, and then laminating the coating sheet (X) and pressing the laminate.

In addition, when a middle sheet (middle layer) is arranged, the method of producing the sheet may include a step of properly laminating a middle sheet (Y) between the sheets so as to be interposed, and then pressing the sheets using, for example, a heated pressure device, or may include a step of applying any one of the base material solutions on the middle sheet as a substrate, and then a step of laminating the other sheet thereon and pressing the laminate.

Using the tooth whitener of the present invention, the composition (A) and the composition (B), or the composition (C) provided as necessary is applied to human oral cavity. The application time of the tooth whitener of the present invention is preferably 10 seconds or more, more preferably 30 seconds or more, even more preferably 1 minute or more, and preferably 8 minute or less, more preferably 4 minute or less for the application time of each composition when the composition (A) or the composition (B) is a dentifrice composition, for example, a toothpaste, or a liquid oral composition, for example, a mouthwash. In addition, when the composition (A) and the composition (B) are dentifrice compositions, for example, a toothpaste, or a liquid oral composition, for example, a mouthwash, the total time for successively applying the composition (A) and the composition (B) each time is preferably 20 seconds or more, more preferably 1 minute or more, even more preferably 2 minutes or more, and preferably 10 minutes or less, more preferably 6 minutes or less, even more preferably 5 minutes or less. When the composition (A) or the composition (B) is a sheet, the application time of each composition is preferably 1 minute or more, preferably 3 minutes or more, and preferably 1 hour or less, more preferably 30 minutes or less, even more preferably 20 minutes or less. In addition, when the composition (A) and the composition (B) are sheets, and one sheet composed of 2 or more layers including one layer of the composition (A) and one layer of the composition (B) is formed, the application time of the sheet is preferably 1 minute or more, more preferably 5 minutes or more, even more preferably 10 minutes or more, and from the viewpoint of ease use for a user, the application time of the sheet is preferably 90 minutes or less, more preferably 60 minutes or less, even more preferably 30 minutes or less.

Furthermore, the application time of the sheet may be the time until the sheet is dissolved in water entirely (dissolution time). The time until the sheet is dissolved in water entirely means a value obtained by measuring a time until the amount of components contained in the sheet is not increased in water after water is applied to the sheet at a speed of 0.1 g/min.

As described above, by applying the composition (A), the composition (B) and the composition (C) as necessary to teeth, it is possible to selectively remove minute solid matters of less than several μm on the tooth enamel surfaces, and thus suppress damage to the tooth enamel itself, smoothen the tooth enamel surface at a level of several ym, and increase reflected light from the enamel surface, and obtain natural gloss of the teeth itself. That is, it is possible to realize the immediately effective gloss imparting effect and the whitening effect. In addition, with application of 1 to 5 times one day preferably for 1 week or more and, for example, 4 weeks or less, that is, even by long-term use or repeated use, it is possible to suppress damage to the tooth enamel surface, and thus it is possible to obtain teeth with natural luster or gloss. Furthermore, when the composition (A), the composition (B) and the composition (C) as necessary are applied to teeth, the time from completion of the application of any one of the compositions to initiation of the application of the following composition is preferably 1 minute or less, more preferably 30 seconds or less.

In relation to the embodiments mentioned above, the present invention further discloses the following tooth whitener and methods of whitening teeth.

[1] A tooth whitens which is provided with a composition (A) and a composition (B) in a separate state, and which is to be used by applying the composition (A) and the composition (B) alternately to teeth wherein:

the composition (A) comprises 0.1% by mass or more and 30% by mass or less of phytic acid or a salt thereof in terms of the acid, does not comprise any polyvalent metal cation, or alternatively comprises such cations in an amount of less than 0.1-fold mol relative to phytic acid or the salt thereof, exhibits a pH of 4 or more and 6.5 or less at 25° C., and comprises a fluoride in an amount such that the mass ratio of the fluoride in terms of fluorine atoms to the phytic acid in terms of the acid (the fluoride in terms of fluorine atoms/phytic acid) is 0.05 or less, or alternatively does not comprise any fluoride, and the composition (B) comprises one or more selected from orthophosphoric acid, condensed phosphoric acid and salts thereof in an amount of 0.01% by mass or more and 15% by mass or less in terms of the acid and exhibits a pH of more than 6.5 and 10.5 or less at 25° C.

[2] The tooth whitener of [1] above, wherein when the composition (A) is a sheet, a content of phytic acid or a salt thereof in the composition (A) is an amount in terms of the acid by dry mass.

[3] The tooth whitener of [1] or [2] above, wherein the content of phytic acid or a salt thereof in the composition (A) is preferably 0.2% by mass or more, more preferably 0.3% by mass or more, and is preferably 20% by mass or less in terms of the acid, and when the composition (A) is a sheet, the content of phytic acid or a salt thereof is preferably 26% by mass or less, more preferably 20% by mass or less, even more preferably 16% by mass or less, and preferably 2% by mass or more, more preferably 5% by mass or more, even more preferably 12% by mass or more (by dry mass) in terms of the acid, or when the composition (A) is a dentifrice composition or a liquid oral composition, the content of phytic acid or a salt thereof is preferably 15% by mass or less, more preferably 5% by mass or less, even more preferably 3% by mass or less, even more preferably 1.5% by mass or less in terms of the acid.

[4] The tooth whitener of any one of [1] to [3] above, wherein the total content of the polyvalent metal cation in the composition (A) is less than 0.1-fold mol, preferably 0.02-fold mol or less, more preferably 0.01-fold mol or less relative to phytic acid.

[5] The tooth whitener of any one of [1] to [4] above, wherein a content of absorbents such as zeolite and activated carbon in addition to a cationic antibacterial agent that is a polyvalent cation other than a polyvalent metal cation in the composition (A) is preferably less than 0.001% by mass, more preferably 0.0001% by mass or less, or the composition (A) does not comprise the absorbents.

[6] The tooth whitener of any one of [1] to [5] above, wherein the pH of the composition (A) is preferably 4.5 or more, and when the composition (A) is a dentifrice composition or a liquid oral composition, the pH of the composition (A) is more preferably 4.8 or more, even more preferably 5 or more, and is preferably 6.2 or less.

[7] The tooth whitener of any one of [1] to [6] above, wherein the composition (A) comprises a fluoride in an amount such that the mass ratio of the fluoride in terms of fluorine atoms to the phytic acid in terms of the acid (the fluoride in terms of fluorine atoms/phytic acid) is preferably 0.03 or less, more preferably 0.01 or less, even more preferably 0.005 or less, even more preferably 0.001 or less.

[8] The tooth whitener of any one of [1] to [7] above, wherein the fluoride of the composition (A) is one or more selected from sodium fluoride, potassium fluoride, ammonium fluoride, stannous fluoride and sodium monofluorophosphate.

[9] The tooth whitener of any one of [1] to [8] above, wherein when the composition (B) is a sheet, a content of the one or more selected from orthophosphoric acid, condensed phosphoric acid and salts thereof in the composition (B) is an amount in terms of the acid by dry mass.

[10] The tooth whitener of any one of [1] to [9] above, wherein a content of the one or more selected from orthophosphoric acid, condensed phosphoric acid and salts thereof in the composition (B) is preferably 0.02% by mass or more, more preferably 0.1% by mass or more, even more preferably 0.5% by mass or more in terms of the acid, and when the composition (B) is a sheet, the content is preferably 1% by mass or more, more preferably 3% by mass or more, even more preferably 5% by mass or more (by dry mass) in terms of the acid, and when the composition (B) is a sheet, the content is preferably 12% by mass or less, more preferably 10% by mass or less, even more preferably 7% by mass or less (by dry mass) in terms of the acid, and when the composition (B) is a liquid oral composition, the content is preferably 7% by mass or less, more preferably 5% by mass or less, even more preferably 3% by mass or less, even more preferably 1% by mass or less in terms of the acid.

[11] The tooth whitener of any one of [1] to [10] above, wherein the condensed phosphoric acid or a salt thereof is preferably one or more selected from pyrophosphoric acid, tripolyphosphoric acid, tetrapolyphosphoric acid, metaphosphoric acid and salts thereof, more preferably one or more selected from sodium pyrophosphate, potassium pyrophosphate, sodium tripolyphosphate and potassium tripolyphosphate, even more preferably one or more selected from pyrophosphoric acid, tripolyphosphoric acid and an alkali metal salt thereof, even more preferably sodium pyrophosphate.

[12] The tooth whitener of any one of [1] to [11] above, wherein the pH of the composition (B) is preferably 7.0 or more, more preferably 7.5 or more, even more preferably 8 or more, and is preferably 10 or less, more preferably 9.5 or less, even more preferably 9 or less.

[13] The tooth whitener of any one of [1] to [12] above, wherein the content of the fluoride in the composition (B) is preferably 0.001% by mass or more, more preferably 0.005% by mass or more, and is preferably 0.2% by mass or less, more preferably 0.15% by mass or less, even more preferably 0.1% by mass or less based on dry mass in the composition (B) in terms of fluorine atoms when the composition (B) is a sheet.

[14] The tooth whitener of any one of [1] to [13] above, wherein the composition (B) is first applied to teeth, and then the composition (A) is applied to teeth.

[15] The tooth whitener of any one of [1] to [13] above, wherein the composition (B) further comprises a fluoride, and the composition (B) is applied to teeth after the composition (A) has been applied to teeth.

[16] The tooth whitener of any one of [1] to [13] above, wherein the tooth whitener is further provided with a composition (C) comprising a fluoride in a separate state, and the composition (C) is applied to teeth after the composition (A) and the composition (B) have been applied to teeth.

[17] The tooth whitener of any one of [13] to [16] above, wherein the fluoride is one or more selected from sodium fluoride, potassium fluoride, ammonium fluoride, stannous fluoride and sodium monofluorophosphate.

[18] The tooth whitener of any one of [1] to [17] above, wherein the composition (A) and the composition (B) are sheets.

[19] The tooth whitener of any one of [1] to [17] above, wherein the composition (A) is a dentifrice composition or a liquid oral composition, and the composition (B) is a dentifrice composition or a liquid oral composition.

[20] The tooth whitener of any one of [1] to [19] above, wherein the phytic acid or a salt thereof of the composition (A) is phytic acid or a sodium salt thereof, and the one or more selected from orthophosphoric acid, condensed phosphoric acid and salts thereof of the composition (B) is preferably one or more selected from pyrophosphoric acid, tripolyphosphoric acid and an alkali metal salt thereof, more preferably sodium pyrophosphate.

[21] The tooth whitener of [20] above, wherein the composition (A) and the composition (B) are sheets, and the sheets are laminated as sheet layers to form one integrated sheet as a laminated sheet.

[22] A method of whitening teeth, which comprises applying a composition (A) and a composition (B) alternately to teeth, wherein:

the composition (A) comprises 0.1% by mass or more and 30% by mass or less of phytic acid or a salt thereof in terms of the acid, does not comprise any polyvalent metal cation, or alternatively comprises such cations in an amount of less than 0.1-fold mol relative to phytic acid or the salt thereof, exhibits a pH of 4 or more and 6.5 or less at 25° C., and comprises a fluoride in an amount such that the mass ratio of the fluoride in terms of fluorine atoms to the phytic acid in terms of the acid (the fluoride in terms of fluorine atoms/phytic acid) is 0.05 or less, or alternatively does not comprise any fluoride, and the composition (B) comprises one or more selected from orthophosphoric acid, condensed phosphoric acid and salts thereof in an amount of 0.01% by mass or more and 15% by mass or less in terms of the acid, and exhibits a pH of more than 6.5 and 10.5 or less at 25° C.

[23] The method of whitening teeth of [22] above, wherein when the composition (A) is a sheet, a content of phytic acid or a salt thereof in the composition (A) is an amount in terms of the acid by dry mass.

[24] The method of whitening teeth of [22] or [23] above, wherein when the composition (B) is a sheet, a content of the one or more selected from orthophosphoric acid, condensed phosphoric acid and salts thereof in the composition (B) is an amount in terms of the acid by dry mass.

[25] The method of whitening teeth of any one of [22] to [24] above, wherein a composition (C) comprising a fluoride is further applied to teeth after the composition (A) and the composition (B) have been applied to teeth.

[26] The method of whitening teeth of any one of [22] to [25] above, wherein the composition (A) and the composition (B) are sheets.

[27] The method of whitening teeth of any one of [22] to [25] above, wherein the composition (A) is a dentifrice composition or a liquid oral composition, and the composition (B) is a dentifrice composition or a liquid oral composition.

[28] The method of whitening teeth of any one of [22] to [27] above, wherein the phytic acid or a salt thereof of the composition (A) is phytic acid or a sodium salt thereof, and the one or more selected from orthophosphoric acid, condensed phosphoric acid and salts thereof of the composition (B) are one or more selected from pyrophosphoric acid, tripolyphosphoric acid and an alkali metal salt thereof.

[29] The method of whitening teeth of [28] above, wherein the composition (A) and the composition (B) are sheets, and the sheets are laminated as sheet layers to form one integrated sheet as a laminated sheet.

[30] The method of whitening teeth of any one of [22] to [29] above, wherein the composition (A) and the composition (B) applied to teeth is the composition (A) and the composition (B) provided in the tooth whitener of any one of [1] to [21] above.

[31] Use of any one of [1] to [21] above for producing a tooth whitener, which is provided with the composition (A) and the composition (B) in a separate state.

[32] Use of the tooth whitener of any one of [1] to [21] above for alternately applying the composition (A) and the composition (B) to teeth.

[33] Use of the tooth whitener of any one of [1] to [21] above for imparting gloss to teeth.

[34] Use of the tooth whitener of any one of [1] to [21] above for whitening teeth.

EXAMPLES

Hereinafter, the present invention will be specifically explained based on Examples. Furthermore, the content of each component represents % by mass unless otherwise indicated in Tables.

Examples 1 to 4

A test solution x and a test solution y of a liquid composition containing phytic acid or condensed phosphoric acid were produced as shown in Table 1. Specifically, the test solution x and the test solution y were produced by dissolving phytic acid or condensed phosphoric acid in purified water, and adjusting pH with a pH regulator to the specific pH of each test solution. Polyvalent metal cations were not blended in any test solution, and polyvalent metal cations such as magnesium, aluminum and calcium in the test solutions were measured by IPC emission spectrometry and were less than 0.02-fold mol relative to phytic acid. Furthermore, the pH of each test solution is a value obtained by measuring the base material solution at 25° C.

Then, the extracted teeth were soaked in deionized water for washing at room temperature (25° C.), and immersed first in the test solution x for 2.5 minutes. Then, the extracted teeth removed from the test solution x was immersed immediately (within 5 seconds) in the test solution y for 2.5 minutes, and the extracted teeth removed from the test solution y was washed with deionized water, and immersed in artificial saliva for about 3 hours. This operation was considered as single treatment, and the treatment was carried out repeatedly 3 times in total. Furthermore, the extracted teeth were human teeth, and three teeth which were not treated to remove stains by abrasion or the like were used for each treatment liquid. As the artificial saliva, an aqueous solution containing calcium chloride (1.0 mM), potassium hydrogen phosphate (0.9 mM) and HEPES (4-(2-hydroxyethyl)-1-piperazineethanesulfonic acid) (2.0 mM) adjusted to pH of 7 by using potassium hydroxide was used.

With respect to the teeth (extracted teeth) after the treatment, each of the evaluations was consequently carried out with the methods described below.

<Evaluation of Tooth Whitening>

Whiteness of the teeth (extracted teeth) after the above-mentioned treatment was evaluated by measuring b* according to the method described below.

Specifically, a digital camera D1x (manufactured by Nikon Corporation) and Ai AF Micro-Nikkor 105 mm F2.8D as a lens and Wireless Remote Speedlight SB-R200 (both manufactured by Nikon Corporation) as a stroboscopic light source were combined and used. The image taken was expressed by the L*a*b* color system using Adobe Photoshop (manufactured by Adobe Systems Incorporated), and the values of b* before and after the treatment by the test solutions were measured. Then, Δb* as a difference in b* before treatment and after treatment {(b* after treatment)−(b* before treatment)} was calculated. A lower value of Δb*, that is, a higher absolute value of Δb*, means whiter color.

The results are shown in Table 1.

<Evaluation of Tooth Gloss>

With respect to the teeth (extracted teeth) after the above-mentioned treatment, the tooth gloss was evaluated by measuring brightness according to the method described below.

Specifically, a method of measuring surface reflected light intensity by image analysis using polarized light, was used. As a device for taking an evaluation image, a digital camera D2x (manufactured by Nikon Corporation) as a camera, Ai AF Micro-Nikkor 105 mm F2.8D as a lens and Wireless Remote Speedlight SB-R200 (both manufactured by Nikon Corporation) as a stroboscopic light source were combined and used. Plastic polarizing films (manufactured by Edmund Optics Inc.) were arranged in front of the light-emitting part of Speedlight and the lens so that the transmission axes would be crossed at a 30-degree angle, and photographs were taken. The average brightness of a highlight part was calculated from the photo image using Adobe Photoshop (manufactured by Adobe Systems Incorporated). A higher value of the brightness means an increase in gloss. The difference in brightness before the treatment and after treatment by the test solutions x and y (brightness after treatment−brightness before treatment) was calculated as Δbrightness. A higher value of the calculated Δbrightness means an increase in gloss.

The results are shown in Table 1.

Comparative Examples 1 to 4

A test solution of a liquid composition containing phytic acid and/or condensed phosphoric acid was produced as shown in Table 1. Polyvalent metal cations were not blended in any test solution, and polyvalent metal cations such as magnesium, aluminum and calcium in the test solutions were measured by IPC emission spectrometry and were less than 0.02-fold mol relative to phytic acid. Furthermore, the pH of each test solution is a value obtained by measuring the base material solution at 25° C.

Then, the extracted teeth were soaked in deionized water for washing at room temperature (25° C.), and immersed in the produced test solution for 5 minutes, and then the extracted teeth removed from the test solution were washed with deionized water, and immersed in the artificial saliva for about 3 hours. This operation was considered as single treatment, and the treatment was carried out repeatedly 3 times. Furthermore, the extracted teeth and the artificial saliva used were similar to those of Example 1.

With respect to the teeth (extracted teeth) after the treatment, each evaluation was carried out in a similar manner to that of Example 1.

The results are shown in Table 1.

TABLE 1

| Composition of solution | Example 1 x | Example 1 y | Example 2 x | Example 2 y | Example 3 x | Example 3 y | Example 4 x | Example 4 y | Comparative Example 1 | Comparative Example 2 | Comparative Example 3 | Comparative Example 4 |
|---|---|---|---|---|---|---|---|---|---|---|---|---|
| Phytic acid Solution (50%) | | 2 | | 2 | 2 | | | 2 | 2 | | 2 | 2 |
| Anhydrous sodium pyrophosphate | 1 | | 1 | | | 1 | 1 | | | 1 | 1 | 1 |
| Hydrochloric acid (35%) | | q.s. | | q.s. | q.s. | | | q.s. | q.s. | | | |
| Sodium hydroxide (48%) | q.s. | | q.s. | | | q.s. | q.s. | | | q.s. | q.s. | q.s. |
| Purified water | Balance | Balance | Balance | Balance | Balance | Balance | Balance | Balance | Balance | Balance | Balance | Balance |
| pH | 9 | 5 | 9 | 6 | 5 | 9 | 7.5 | 5 | 6 | 9 | 6 | 9 |
| Δb* | −1.60 | | −1.48 | | −1.27 | | −1.01 | | −0.31 | −0.15 | −0.59 | −0.09 |
| ΔBrightness | 7 | | 9 | | 6 | | 5 | | 1 | 2 | 3 | 1 |
| Amount of pyrophosphoric acid in terms of the acid | 0.67 | | 0.67 | | | 0.67 | 0.67 | | | 0.67 | 0.67 | 0.67 |
| Amount of phytic acid in terms of the acid | | 1 | | 1 | 1 | | | 1 | 1 | | 1 | 1 |

Examples 5 to 8

A test solution x and a test solution y of a liquid composition containing phytic acid or condensed phosphoric acid were produced as shown in Table 2. Polyvalent metal cations were not blended in any test solution, and polyvalent metal cations such as magnesium, aluminum and calcium in the test solutions were measured by IPC emission spectrometry and were less than 0.02-fold mol relative to phytic acid.

Furthermore, the pH of each test solution is a value obtained by measuring the base material solution at 25° C.

Then, extracted teeth were used in a similar manner to that of Example 1, and then subjected to similar treatment as using the test solution x and the test solution y, and then using the teeth (extracted teeth) after the treatment, the evaluation of tooth whitening was carried out according to the method described above.

The results are shown in Table 2.

TABLE 2

| Composition of solution | Example 5 x | Example 5 y | Example 6 x | Example 6 y | Example 7 x | Example 7 y | Example 8 x | Example 8 y |
|---|---|---|---|---|---|---|---|---|
| Phytic acid Solution (50%) | | 2 | | 30 | | 0.6 | | 2 |
| Anhydrous sodium pyrophosphate | 1 | | 6.5 | | 0.05 | | | |
| Sodium tripolyphosphate | | | | | | | 1 | |
| Hydrochloric acid (35%) | | q.s. | | q.s. | | q.s. | | q.s. |
| Sodium hydroxide (48%) | q.s. | | q.s. | | q.s. | | q.s. | |
| Purified water | Balance | Balance | Balance | Balance | Balance | Balance | Balance | Balance |
| pH | 9 | 5.5 | 9 | 5 | 9 | 5 | 9 | 5 |
| Δb* | −1.25 | | −1.04 | | −0.90 | | −1.23 | |
| Amount of pyrophosphoric acid in terms of the acid | 0.67 | | 4.35 | | 0.033 | | | |
| Amount of phytic acid in terms of the acid | | 1 | | 15 | | 0.3 | | 1 |
| Amount of tripolyphosphoric acid in terms of the acid | | | | | | | 0.7 | |

According to the results of Tables 1 to 2, it is found that all of Examples 1 to 8 exerts an excellent tooth whitening effect with short term treatment in comparison to Comparative Examples 1 to 2 in which only either a composition containing phytic acid or a composition containing pyrophosphoric acid was applied alone, and Comparative Examples 3 to 4 in which a composition containing both of phytic acid and pyrophosphoric acid was applied. In addition, it was confirmed that the tooth whitener of the present invention can also impart excellent gloss to teeth.

Examples 9-1 to 9-5

A base material solution containing condensed phosphoric acid was produced, and pullulan was blended to produce a sheet x (8 μm thickness, 9 g/m² basis weight) as shown in Table 3. Similarly, a base material solution containing phytic acid was produced, and pullulan was blended to produce a sheet y (55 μm thickness, 72 g/m² basis weight), and the sheet y was laminated on one side of the sheet x. Furthermore, a layer containing 65% ethylcellulose and 35% polyethylene glycol (PEG600) was laminated on the surface of the sheet y. Polyvalent metal cations were not blended in any base material solution, and polyvalent metal cations such as magnesium, aluminum and calcium in the base material solution were measured by IPC emission spectrometry and were less than 0.02-fold mol relative to phytic acid. Furthermore, the pH of each sheet was a value obtained by measuring the base material solution, and the thicknesses of the sheets x and y were determined on the basis of entire dissolution of the sheets for 10 minutes after the attachment.

Then, the extracted teeth were soaked in deionized water for washing at room temperature (25° C.), the laminated sheet was attached to the teeth so that the side exposing the sheet x of the laminated sheet was in contact with the teeth, and immediately after the attachment, a 20 mm sponge (communicative-porous sponge MAPS K001 manufactured by INOAC CORPORATION) supplying artificial saliva at a speed of 0.1 g/min was brought into contact with the opposite side to the side in contact with the teeth. Then, remaining wreck of the sheet was removed with light brushing, and then the extracted teeth were immersed in the artificial saliva for about 3 hours. This operation was considered as single treatment, and the treatment was carried out repeatedly 3 times. Furthermore, the extracted teeth and the artificial saliva used were similar to those of Example 1.

With respect to the teeth (extracted teeth) after the treatment, evaluations were carried out in a similar manner to that of Example 1.

The results are shown in Table 3.

TABLE 3

| Component | Example 9-1 x | Example 9-1 y | Example 9-2 x | Example 9-2 y | Example 9-3 x | Example 9-3 y | Example 9-4 x | Example 9-4 y | Example 9-5 x | Example 9-5 y |
|---|---|---|---|---|---|---|---|---|---|---|
| Phytic acid | | 15.4 | | 15 | | 15 | | 15 | | 26 |
| Anhydrous sodium pyrophosphate | 7.9 | | 8 | | 8 | | 8 | | 12 | |
| Hydrochloric acid | | q.s. | | q.s. | | q.s. | | q.s. | | q.s. |
| Sodium hydroxide | q.s. | | q.s. | | q.s. | | q.s. | | q.s. | |
| Glycerin | 18.8 | 15.2 | 20 | 15 | 20 | 15 | 20 | 15 | 20 | 15 |
| Flavor | 0.8 | 0.7 | 1 | 1 | 1 | 1 | 1 | 1 | 1 | 1 |
| Polyglyceryl monomyristate | 1.8 | 1.8 | 2.5 | 2.5 | 2.5 | 2.5 | 2.5 | 2.5 | 2.5 | 2.5 |
| Pullulan | Balance | Balance | Balance | Balance | Balance | Balance | Balance | Balance | Balance | Balance |
| pH | 9 | 4.5 | 9 | 4.5 | 7.5 | 5.5 | 9.5 | 6 | 9 | 4.5 |
| Δb* | −1.59 | | −1.55 | | −1.32 | | −0.87 | | −2.16 | |
| ΔBrightness | 5 | | 5 | | 4.1 | | 1 | | 1.5 | |
| Amount of pyrophosphoric acid in terms of the acid | 5.29 | | 5.35 | | 5.35 | | 5.35 | | 8.03 | |
| Amount of phytic acid in terms of the acid | | 15.4 | | 15 | | 15 | | 15 | | 26 |

From the results of Table 3, it was confirmed that a sheet of the composition (A) and the composition (B) laminated as respective sheet layers can also bring the immediately effective, excellent tooth whitening effect.

Example 10

A toothpaste x and a toothpaste y containing phytic acid or condensed phosphoric acid were produced by mixing each of the components as shown in Table 4. The obtained toothpaste x was applied to the oral cavity, the toothpaste was discharged from the mouth, then the toothpaste y was applied immediately (within 30 seconds), and thereby excellent tooth whitening effect and gloss imparting effect were obtained. Furthermore, the pH of the toothpastes x and y is a value obtained by measuring when diluted to 30% by mass with water at 25° C.

TABLE 4

| Component | Example 10 x | Example 10 y |
|---|---|---|
| Phytic acid | | 0.3 |
| Anhydrous sodium pyrophosphate | 0.4 | |
| Erythritol | 40 | 40 |
| Glycerin | 8 | 8 |
| Sorbitol Solution (70%) | 26 | 26 |
| Silica | 10 | 10 |
| Polyethylene glycol (MW = 600) | 3 | 3 |
| Sodium carboxymethylcellulose | 0.6 | 0.6 |
| Xanthan gum | 0.1 | 0.1 |
| Sodium saccharin | 0.05 | 0.05 |
| Sodium lauryl sulfate | 1.5 | 1.5 |
| Flavor | 1 | 1 |
| Hydrochloric acid (35%) | q.s. | |
| Sodium hydroxide (48%) | | q.s. |

TABLE 4-continued

|  | Example 10 | |
| --- | --- | --- |
| Component | x | y |
| Purified water | Balance | Balance |
| Total | 100 | 100 |
| pH | 9 | 6 |
| Amount of pyrophosphoric acid in terms of the acid | 0.27 | |
| Amount of phytic acid in terms of the acid | | 0.3 |

Example 11

A mouthwash x and a mouthwash y containing phytic acid or condensed phosphoric acid were produced by mixing each of the components as shown in Table 5. The obtained mouthwash x was applied to the oral cavity, then the mouthwash y was applied immediately (within 130 seconds), and thereby an excellent tooth whitening effect and a gloss imparting effect were obtained.

TABLE 5

|  | Example 11 | |
| --- | --- | --- |
| Component | x | y |
| Phytic acid | | 0.3 |
| Anhydrous sodium pyrophosphate | 0.3 | |
| Erythritol | 4 | 4 |
| Sorbitol (70%) | 4 | 4 |
| Glycerin | 1 | 1 |
| Ethanol | 5 | 5 |
| Polyoxyethylene hydrogenated castor oil | 0.5 | 0.5 |
| Flavor | 0.15 | 0.15 |
| Sucralose | 0.006 | 0.006 |
| Hydrochloric acid (35%) | q.s. | |
| Sodium hydroxide (48%) | | q.s. |
| Purified water | Balance | Balance |
| Total | 100 | 100 |
| pH | 9 | 6 |
| Amount of pyrophosphoric acid in terms of the acid | 0.20 | |
| Amount of phytic acid in terms of the acid | | 0.3 |

Examples 12 to 16

A test solution x and a test solution y of a liquid composition containing phytic acid or condensed phosphoric acid were produced, and a test solution z of a liquid composition was further produced in Example 13 as shown in Table 6. Polyvalent metal cations were not blended in any test solution, and polyvalent metal cations such as magnesium, aluminum and calcium in the test solution were measured by IPC emission spectrometry and were less than 0.02-fold mol relative to phytic acid. Furthermore, the pH of each test solution is a value obtained by measuring the base material solution at 25° C.

Then, using extracted teeth is used in a similar manner to that of Example 1, and subjected to similar treatment as using the test solution x and the test solution y, and then using the teeth (extracted teeth) after the treatment, evaluations of the tooth whitening effect and gloss imparting effect were carried out according to the methods described above.

The results are shown in Table 6.

TABLE 6

| Composition of solution | Example 12 | | Example 13 | | | Example 14 | | Example 15 | | Example 16 | |
| --- | --- | --- | --- | --- | --- | --- | --- | --- | --- | --- | --- |
|  | x | y | x | y | z | x | y | x | y | x | y |
| Phytic acid Solution (50%) | | 2 | | 2 | | | 2 | | 2 | | 2 |
| Anhydrous sodium pyrophosphate | 1 | | 1 | | | 1 | | 1 | | 1 | |
| Sodium fluoride | 0.21 | | | | 0.21 | | | 0.0022 | | | |
| Magnesium chloride•hexahydrate | | | | | | | 0.0031 | | | | |
| Hydrochloric acid (35%) | q.s. | | q.s. | | q.s. | q.s. | | q.s. | | q.s. | |
| Sodium hydroxide (48%) | | q.s. | | q.s. | | | q.s. | | q.s. | | q.s. |
| Purified water | Balance | Balance | Balance | Balance | Balance | Balance | Balance | Balance | Balance | Balance | Balance |
| pH | 9 | 5 | 9 | 5 | 8.5 | 9 | 6 | 9 | 6 | 9.5 | 5 |
| Δb* | -1.15 | | -1.53 | | | -1.11 | | -1.16 | | -1.09 | |
| ΔBrightness | 4 | | 6 | | | 4 | | 7 | | 5 | |
| Amount of pyrophosphoric acid in terms of the acid | 0.67 | | 0.67 | | | 0.67 | | 0.67 | | 0.67 | |
| Amount of phytic acid in terms of the acid | | 1 | | 1 | | | 1 | | 1 | | 1 |

From the results of Table 6, it was confirmed that all of Example 12 containing sodium fluoride in the composition (B), and Example 13 containing sodium fluoride in the composition (C) had an excellent whitening effect and high gloss. In addition, it was confirmed that Example 14 containing 0.01-fold mol polyvalent metal in the composition (A), and Example 15 containing 0.001-fold sodium fluoride in the mass ratio to phytic acid in terms of the acid in the composition (A) had a slighter whitening effect and less gloss in comparison to Example 2, but more excellent whitening effect and gloss effect in comparison to Comparative Examples.

What is claimed is:

1. A method of whitening teeth, which comprises applying a composition (A) and a composition (B) alternately to teeth, wherein the composition (A) comprises from 0.1% by mass to 30% by mass of phytic acid or a salt thereof in terms of the acid, does not comprise any polyvalent metal cation, or alternatively comprises such cations in an amount of less than 0.1-fold mol relative to phytic acid or the salt thereof, exhibits a pH of 4 or more and 6.5 or less at 25° C., and comprises a fluoride in an amount such that the mass ratio of the fluoride in terms of fluorine atoms to the phytic acid in terms of the acid (the fluoride in terms of fluorine atoms/phytic acid) is 0.05 or less, or alternatively does not comprise any fluoride, and the composition (B) comprises one or more selected from orthophosphoric acid, condensed phosphoric acid and salts thereof in an amount of from 0.01% by mass to 15% by mass in terms of the acid and exhibits a pH of more than 6.5 and 10.5 or less at 25° C., wherein the time from completion of the application of any one of the compositions to initiation of the application of the following composition is 3 minutes or less;

and wherein ΔBrightness is at least 5.

2. The method of whitening teeth according to claim 1, wherein the fluoride of the composition (A) is one or more selected from sodium fluoride, potassium fluoride, ammonium fluoride, stannous fluoride and sodium monofluorophosphate.

3. The method of whitening teeth according to claim 1, wherein the composition (A) is first applied to teeth, and then the composition (B) is applied to the teeth.

4. The method of whitening teeth according to claim 1, wherein the composition (B) further comprises a fluoride, and the composition (B) is applied to teeth after the composition (A) has been applied.

5. The method of whitening teeth according to claim 1, wherein a composition (C) comprising a fluoride is further applied to the teeth after the composition (A) and the composition (B) have been applied to the teeth.

6. The method of whitening teeth according to claim 4, wherein the fluoride is one or more selected from sodium fluoride, potassium fluoride, ammonium fluoride, stannous fluoride and sodium monofluorophosphate.

7. The method of whitening teeth according to claim 1, wherein the condensed phosphoric acid or a salt thereof of the composition (B) is pyrophosphoric acid or a salt thereof.

8. The method of whitening teeth according to claim 1, wherein the phytic acid or a salt thereof of the composition (A) is phytic acid or a sodium salt thereof, and the one or more selected from orthophosphoric acid, condensed phosphoric acid and salts thereof of the composition (B) are one or more selected from pyrophosphoric acid, tripolyphosphoric acid and an alkali metal salt thereof.

9. The method of whitening teeth according to claim 1, wherein the composition (A) and the composition (B) are sheets.

10. The method of whitening teeth according to claim 1, wherein the composition (A) is a dentifrice composition or a liquid oral composition, and the composition (B) is a dentifrice composition or a liquid oral composition.

11. The method of whitening teeth according to claim 1, wherein the composition (A) and the composition (B) are sheets, and the sheets are laminated as sheet layers to form one integrated sheet as a laminated sheet.

12. The method of claim 1, wherein composition (A) and composition (B) are dentifrice compositions.

13. The method of claim 12, wherein the time of application for each composition is from 10 seconds to 8 minutes.

14. The method of claim 12, wherein the total time for one application of composition (A) and composition (B) is from 20 seconds to 10 minutes.

15. The method of claim 11, wherein the application time of each composition (A) and (B) is from 1 minute to 90 minutes.

16. The method of claim 1, wherein composition (A) and composition (B) are alternatively applied to teeth 1 to 5 times a day.

17. The method of claim 16, wherein composition (A) and composition (B) are alternatively applied to teeth 1 to 5 times a day for 1 to 4 weeks.

* * * * *